(12) United States Patent
Mattsby-Baltzer et al.

(10) Patent No.: US 7,928,185 B2
(45) Date of Patent: Apr. 19, 2011

(54) SYNTHETIC ARGININE SUBSTITUTED PEPTIDES AND THEIR USE

(75) Inventors: Inger Mattsby-Baltzer, Göteborg (SE); Gunnar Dolphin, Lepoint de Beauvoixin (FR)

(73) Assignee: PharmaSurgics in Sweden AB, Göteborg (SE)

( * ) Notice: Subject to any disclaimer, the term of this patent is extended or adjusted under 35 U.S.C. 154(b) by 171 days.

(21) Appl. No.: 12/292,030

(22) Filed: Nov. 10, 2008

(65) Prior Publication Data

US 2009/0186823 A1     Jul. 23, 2009

Related U.S. Application Data

(60) Provisional application No. 60/990,066, filed on Nov. 26, 2007.

(30) Foreign Application Priority Data

Nov. 14, 2007  (EP) ..................................... 07120713

(51) Int. Cl.
  *C07K 5/00*   (2006.01)
  *A61K 38/00*  (2006.01)
(52) U.S. Cl. ......... 530/300; 530/326; 530/345; 514/1.1; 514/2.4; 514/2.5
(58) Field of Classification Search ........................ None
See application file for complete search history.

(56) References Cited

FOREIGN PATENT DOCUMENTS

| | | |
|---|---|---|
| JP | 07-145196 | 6/1995 |
| JP | 07-274970 | 10/1995 |
| JP | 08-040925 | 2/1996 |
| JP | 08-143468 | 6/1996 |
| WO | WO01/34641 A | 5/2001 |

OTHER PUBLICATIONS

Chapple et al., Infect. Immun., 1998, vol. 66(6):2434-2440.*
Odell et al., FEBS Lett., 1996, vol. 382(1-2):175-178.*
Bellamy et al., Biochim. Biophys. Acta, 1992, vol. 1121(1-2):130-136.*
European Patent Office Communication dated Apr. 17, 2008.
Odell, E.W. et al.: "Antibacterial Activity of Peptides Homologous to a Loop Region in Human Lactoferrin", Febs Letters, Elsevier, Amsterdam, NL, vol. 382, 1996, pp. 175-178.
Van Berkel, P.H.C. et al.: "N-Terminal Stretch ARG2, ARG3, ARG4 and ARG5 of Human Lactoferrin Is Essential for Binding to Heparin, Bacterial Lipopolysaccharide, Human Lysozyme and DNA", Biochemical Journal, Portland Press, London, GB, vol. 328, Nov. 15, 1997, pp. 145-151.
Azuma, M. et al.: "Antibacterial activity of multiple antigen peptides homologous to a loop region in human lactoferrin", Journal of Peptide Research, vol. 54, No. 3, Sep. 1999, pp. 237-241.
Moriarty, L.C. et al.: "Factors contributing to the potency of antimicrobial cationic peptides from the N-terminal region of human lactoferrin", FEMS Microbiology Letters, Amsterdam, ML, vol. 239, No. 2, Oct. 15, 2004, pp. 295-299.
Lönnerdal, B.: "Lactoferrin Receptors in Intestinal Brush Border Membranes," Lactoferrin: Structure and Function, ed. T.W. Hutchens et al., Plenum Press, Nyew Yor, 1994, pp. 171-175.
Bellamy, W. et al.: "Identification of the bactericidal domain of lactoferrin," Biochimica et Biophysica Acta, 1121 (1992), pp. 130-136, Elsevier Science Publishers B.V.
Bellamy, W. et al.: "Antibacterial spectrum of lactoferrin B, a potent bactericidal peptide derived from the N-terminal region of bovine lactoferrin," J. Applied Bacteriology 1992, 73, pp. 472-479.

* cited by examiner

*Primary Examiner* — Elizabeth C. Kemmerer
*Assistant Examiner* — Xiaozhen Xie
(74) *Attorney, Agent, or Firm* — Buchanan Ingersoll & Rooney PC

(57) ABSTRACT

The present invention relates to new arginine substituted peptides designed based on the sequence of human lactoferrin and to use thereof, in particular for treatment and/or prevention of infections, inflammations, tumours, pain, wounds and/or scars.

8 Claims, 7 Drawing Sheets

SEQUENCE LISTING

<160> NUMBER OF SEQ ID NOS: 12

<210> SEQ ID NO 1
<211> LENGTH: 11
<212> TYPE: PRT
<213> ORGANISM: Artificial
<220> FEATURE:
<223> OTHER INFORMATION: a fragment of human lactoferrin
      corresponding to aa 21-31

<400> SEQUENCE: 1

Phe Gln Trp Gln Arg Asn Met Arg Lys Val Arg
1               5                   10

<210> SEQ ID NO 2
<211> LENGTH: 31
<212> TYPE: PRT
<213> ORGANISM: Artificial
<220> FEATURE:
<223> OTHER INFORMATION: a fragment of human lactoferrin
      corresponding to aa 1-31

<400> SEQUENCE: 2

Gly Arg Arg Arg Arg Ser Val Gln Trp Cys Ala Val Ser Gln Pro Glu
1               5                   10                  15

Ala Thr Lys Cys Phe Gln Trp Gln Arg Asn Met Arg Lys Val Arg
            20                  25                  30

<210> SEQ ID NO 3
<211> LENGTH: 20
<212> TYPE: PRT
<213> ORGANISM: Artificial
<220> FEATURE:
<223> OTHER INFORMATION: a fragment of human lactoferrin corresponding
      to aa 1-20

<400> SEQUENCE: 3

Gly Arg Arg Arg Arg Ser Val Gln Trp Cys Ala Val Ser Gln Pro Glu
1               5                   10                  15

Ala Thr Lys Cys
            20

<210> SEQ ID NO 4
<211> LENGTH: 8
<212> TYPE: PRT
<213> ORGANISM: Artificial
<220> FEATURE:
<223> OTHER INFORMATION: a fragment of human lactoferrin corresponding
      to aa 33-40

<400> SEQUENCE: 4

Pro Pro Val Ser Cys Ile Lys Arg
1               5

<210> SEQ ID NO 5
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)

-continued

```
<223> OTHER INFORMATION: AMIDATION

<400> SEQUENCE: 5

Phe Gln Trp Gln Arg Asn Met Arg Lys Val Arg Gly Ser Arg Arg
1               5                   10                  15

Arg Gly

<210> SEQ ID NO 6
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: ACETAMIDOMETYL-CYS
<220> FEATURE:
<221> NAME/KEY: MOD_RES
<222> LOCATION: (22)..(22)
<223> OTHER INFORMATION: AMIDATION

<400> SEQUENCE: 6

Ala Thr Lys Cys Phe Gln Trp Gln Arg Asn Met Arg Lys Val Arg Gly
1               5                   10                  15

Ser Arg Arg Arg Arg Gly
            20

<210> SEQ ID NO 7
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)
<223> OTHER INFORMATION: AMIDATION

<400> SEQUENCE: 7

Phe Gln Trp Lys Arg Asn Met Arg Lys Val Arg Gly Ser Arg Arg
1               5                   10                  15

Arg Gly

<210> SEQ ID NO 8
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: ACETAMIDOMETYL-CYS
<220> FEATURE:
<221> NAME/KEY: MOD_RES
<222> LOCATION: (22)..(22)
<223> OTHER INFORMATION: AMIDATION

<400> SEQUENCE: 8

Ala Thr Lys Cys Phe Gln Trp Lys Arg Asn Met Arg Lys Val Arg Gly
1               5                   10                  15

Ser Arg Arg Arg Arg Gly
            20
```

```
<210> SEQ ID NO 9
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)
<223> OTHER INFORMATION: AMIDATION

<400> SEQUENCE: 9

Phe Gln Trp Lys Arg Ala Met Arg Lys Val Arg Gly Ser Arg Arg
1               5                   10                  15

Arg Gly

<210> SEQ ID NO 10
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: ACETAMIDOMETYL-CYS
<220> FEATURE:
<221> NAME/KEY: MOD_RES
<222> LOCATION: (22)..(22)
<223> OTHER INFORMATION: AMIDATION

<400> SEQUENCE: 10

Ala Thr Lys Cys Phe Gln Trp Lys Arg Ala Met Arg Lys Val Arg Gly
1               5                   10                  15

Ser Arg Arg Arg Arg Gly
            20

<210> SEQ ID NO 11
<211> LENGTH: 15
<212> TYPE: PRT
<213> ORGANISM: Artificial
<220> FEATURE:
<223> OTHER INFORMATION: fragment of human lactoferrin corresponding
      to aa 6-20

<400> SEQUENCE: 11

Ser Val Gln Trp Cys Ala Val Ser Gln Pro Glu Ala Thr Lys Cys
1               5                   10                  15

<210> SEQ ID NO 12
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa can be Gln or Lys
<220> FEATURE:
<221> NAME/KEY: MISC_FEATURE
```

```
<222> LOCATION: (6)..(6)
<223> OTHER INFORMATION: Xaa can be Asn or Ala

<400> SEQUENCE: 12

Phe Gln Trp Xaa Arg Xaa Met Arg Lys Val Arg Gly Ser Arg Arg Arg
1               5                   10                  15

Arg Gly
```

US 7,928,185 B2

SYNTHETIC ARGININE SUBSTITUTED PEPTIDES AND THEIR USE

The present application claims benefit of priority from U.S. Provisional Application No. 60/990,066, filed 26 Nov. 2007. This application also claims priority from a foreign application EP 07120713.8, filed 14 Nov. 2007. The entire content of these applications is hereby incorporated by reference.

FIELD OF THE INVENTION

The present invention relates to new peptides and to use thereof, in particular for treatment and/or prevention of infections, inflammations and/or tumours.

BACKGROUND ART

Lactoferrin is a single chain metal-binding glycoprotein with a molecular weight of 77 kd. It has been found that the structural domain of lactoferrin responsible for the bactericidal properties is a pepsin-cleaved fragment called lactoferricin (see e.g. Bellamy W., et al., Identification of the bactericidal domain of lactoferrin, Biochim. Biophys. Acta 1121: 130-136, 1992, and Bellamy W., et al., Antibacterial spectrum of lactoferricin B, a potent bactericidal peptide derived from the N-terminal region of bovine lactoferrin, J. Appl. Bact. 73: 472-479, 1992).

Lactoferrin receptors are found on many types of cells including monocytes and macrophages, lectin-stimulated human peripheral blood lymphocytes, brushborder cells, and tumour cell lines.

Several patent publications describe the possible use of lactoferrin for treatment of infections or inflammations. In WO 98/06425, e.g., it is disclosed that lactoferrin and lactoferricin can be used for treatment and prevention of infections, inflammations and tumours.

EP 629 347 describes an antimicrobial agent containing (A) lactoferrin hydrolysate and/or one or more of antimicrobial peptides derived from lactoferrins, and (B) one or more compounds selected from the group consisting of metal-chelating protein, tocopherol, cyclodextrin, glycerine-fatty acid ester, alcohol, EDTA or a salt thereof, ascorbic acid or a salt thereof, citric acid or a salt thereof, polyphosphoric acid or a salt thereof, chitosan, cysteine, and cholic acid as the effective components thereof. This antimicrobial agent is intended for treatment of products, and especially for safely treating e.g. food and medicines. The agent according to this publication is thus a new preservative. In the publication several peptide sequences are given and some of them resemble the peptides according to the invention, although there are several important differences described further below.

U.S. Pat. No. 5,304,633 discloses antimicrobial peptides isolated from hydrolysates of human and bovine lactoferrin. Isolation of peptides corresponding to amino acids 12 to 47, and 17 to 41 of human lactoferrin are specifically disclosed.

JP 7145196 describes the preparation of antibiotic peptides by hydrolysis of lactoferrin. The preparation of a peptide corresponding to amino acids 17 to 41 of human lactoferrin is specifically described.

JP 8040925 discloses pharmaceutical compositions containing lactoferrin derived peptides and their use in the treatment of cornea damages, especially keratitis. Peptides corresponding to amino acids 17 to 41, 12 to 58, and 19 to 38, of human lactoferrin are specifically disclosed JP 7274970 describes the recombinant production of antibacterial lactoferricin derived peptides, specifically a peptides corresponding to amino acids 18 to 42 of human lactoferrin is disclosed.

JP 8143468 describes lactoferrin derived peptides and their use as antiulcer drugs, a peptide corresponding to amino acids 19 to 33 of human lactoferrin is specifically disclosed.

WO 00/01730 describes peptides derived from human lactoferrin and their use for treatment of infections and inflammations.

EP 1 228 097 describes peptides derived from the immediate N-terminal end of human lactoferrin and their use as microbial agents.

EP 1151009 describes peptides comprising a sequence corresponding to amino acids 35 to 50 of human lactoferrin having antimicrobial and/or endotoxin neutralizing activity.

WO 2006/047744 describes immunomodulatory peptides derived from the N-terminal part of human lactoferrin comprising at least 33 amino acids and being substituted in both the N- and C-terminus with four positively charged amino acids.

SUMMARY OF THE INVENTION

The object of the present invention is to provide new synthetic peptides which can be used for the same purposes as lactoferrin, lactoferricin or other lactoferrin derived peptides and which will have the same, or better, effects although having production, technical and/or biochemical advantages.

The aim of the studies leading to the present invention was to design new peptides which should essentially be as efficient as, or preferably more efficient than, human lactoferrin, human lactoferricin and other lactoferrin derived peptides in treatment and prevention of infections, inflammations, tumours, wounds, and scars.

It was found that peptides formed of the sequences constituted of all or some of the amino acids 21-31 of human lactoferrin counted from the N-terminal end, further substituted with arginine containing peptides, have the desired properties.

According to the present invention, it is shown that the peptides designed based on the sequence constituted of amino acids 21-31 from the N-terminal end of human lactoferrin, substituted with arginine containing peptides, have the desired properties.

It has been shown that humans in their brush border membrane have receptors which can bind to human lactoferrin (see e.g. Lonnerdal B., Lactoferrin receptors in intestinal brush border membranes, Adv. Exp. Med. Biol. 1994, 357: 171-175). It has also been shown that bovine lactoferrin does not bind to these receptors. A plausible mechanism for the uptake of these new peptides in the human body is that the peptides are taken up through binding to cellular receptors. However, the invention is in no way limited to this mechanism.

Thus, the present invention relates to new synthetic peptides and to functionally equivalent homologues or analogues thereof.

Furthermore, the invention relates to medicinal products and to food stuff, especially infant formula food, comprising said peptides.

The invention also relates to use of said peptides for the production of medicinal products for treatment and prevention of infections, inflammations and tumours.

The peptides according to the invention are fungicidal and bactericidal, and can thus be used for other applications when substances with such properties are desired. They may for example be used as preservatives.

The characterising features of the invention will be evident from the following description and the appended claims.

DETAILED DESCRIPTION OF THE INVENTION

Thus, the present invention relates to peptides designed based on the amino acid sequence of fragments of the protein human lactoferrin (hLF). The fragment of hLF that is used as a basis for the invention is constituted by the amino acids in positions 21-31 of hLF, the sequence of which is:

```
                                    (SEQ ID NO: 1)
Phe-Gln-Trp-Gln-Arg-Asn-Met-Arg-Lys-Val-Arg
```

In the description single-letter or three-letter symbols are used to denote the amino acids. These symbols, which are well known to man skilled in the art, have the following meaning: A=Ala=alanine, C=Cys=cysteine, D=Asp=aspartic acid, E=Glu=glutamic acid, F=Phe=phenylalanine, G=Gly=glycine, I-Ile=isoleucine, K=Lys=lysine, M=Met=methionine, N=Asn=asparagine, P=Pro=proline, Q=Gln=glutamine, R=Arg=arginine, S=Ser=serine, T=Thr=threonine, V=Val=valine, W=Trp=tryptophan, Orn=Ornithine, Nle=Norleucine and X=Xaa=a variable amino acid. Ac and $NH_2$ in some of the sequences denote an acetyl ($CH_3CO$—) group and an amino group, respectively, that have been used to modify the amino and the carboxy terminals of the peptides.

The N-terminal part of human lactoferrin contains an arginine rich sequence, as shown below for the sequence of amino acids 1-31 of human lactoferrin:

```
                                    (SEQ ID NO: 2)
Gly-Arg-Arg-Arg-Arg-Ser-Val-Gln-Trp-Cys-Ala-Val-

Ser-Gln-Pro-Glu-Ala-Thr-Lys-Cys-Phe-Gln-Trp-Gln-

Arg-Asn-Met-Arg-Lys-Val-Arg
```

The sequence Gly-Arg-Arg-Arg-Arg-Ser was identified as an important sequence motif and was used in the design of the peptides of the invention.

The present invention relates to peptides according to formula (I)

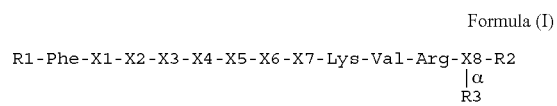

Formula (I)

wherein amino acid X1 is Gln or Ala, amino acid X2 is Trp or Leu, amino acid X3 is Gln, Ala, Orn, Nle or Lys, amino acid X4 is Arg, Ala or Lys, amino acid X5 is Asn, Ala, Orn or Nle, amino acid X6 is Met, Ala or Leu, amino acid X7 is Arg, Ala or Lys, amino acid X8 is Gly, Lys, Glu or Asp;

when X8 is Gly then R3 is Ser-$(Arg)_n$-X9 and the bond α is a peptide bond between the carboxyl group of Gly and the amino group of Ser;

when X8 is Lys then R3 is X9-$(Arg)_n$-Ser and the bond α is an amide bond between the ε-amino group in Lys and the carboxyl group in Ser; and when X8 is Glu or Asp then R3 is Ser-$(Arg)_n$-X9 and the bond α is an amide bond between the γ-carboxyl group of Glu or the β-carboxyl group of Asp and the amino group of Ser;

amino acid X9 is either no amino acid or Gly;

and n is an integer from 1 to 10, preferably an integer from 2 to 6, preferably an integer from 4 to 6, or even more preferably an integer from 3 to 4;

R1 is either no amino acid, Cys or a peptide sequence selected from the peptides SEQ ID NO: 3 and N-terminally truncated fragments thereof including

```
Gly-Arg-Arg-Arg-Arg-Ser-Val-Gln-Trp-Cys-Ala-Val-Ser-Gln-Pro-Glu-Ala-Thr-Lys-Cys,

Arg-Arg-Arg-Arg-Ser-Val-Gln-Trp-Cys-Ala-Val-Ser-Gln-Pro-Glu-Ala-Thr-Lys-Cys,

Arg-Arg-Arg-Ser-Val-Gln-Trp-Cys-Ala-Val-Ser-Gln-Pro-Glu-Ala-Thr-Lys-Cys,

Arg-Arg-Ser-Val-Gln-Trp-Cys-Ala-Val-Ser-Gln-Pro-Glu-Ala-Thr-Lys-Cys,

Arg-Ser-Val-Gln-Trp-Cys-Ala-Val-Ser-Gln-Pro-Glu-Ala-Thr-Lys-Cys,

Ser-Val-Gln-Trp-Cys-Ala-Val-Ser-Gln-Pro-Glu-Ala-Thr-Lys-Cys,

Val-Gln-Trp-Cys-Ala-Val-Ser-Gln-Pro-Glu-Ala-Thr-Lys-Cys,

Gln-Trp-Cys-Ala-Val-Ser-Gln-Pro-Glu-Ala-Thr-Lys-Cys,

Trp-Cys-Ala-Val-Ser-Gln-Pro-Glu-Ala-Thr-Lys-Cys,

Cys-Ala-Val-Ser-Gln-Pro-Glu-Ala-Thr-Lys-Cys,

Ala-Val-Ser-Gln-Pro-Glu-Ala-Thr-Lys-Cys,

Val-Ser-Gln-Pro-Glu-Ala-Thr-Lys-Cys,

Ser-Gln-Pro-Glu-Ala-Thr-Lys-Cys,

Gln-Pro-Glu-Ala-Thr-Lys-Cys,

Pro-Glu-Ala-Thr-Lys-Cys,

Glu-Ala-Thr-Lys-Cys,
```

```
                        Ala-Thr-Lys-Cys,

Thr-Lys-Cys, and

Lys-Cys,
```

Preferably R1 is either no amino acid, Cys or a peptide sequence selected from the peptides SEQ ID NO: 11 and N-terminally truncated fragments thereof including

```
Ser-Val-Gln-Trp-Cys-Ala-Val-Ser-Gln-Pro-Glu-Ala-Thr-Lys-Cys,

Val-Gln-Trp-Cys-Ala-Val-Ser-Gln-Pro-Glu-Ala-Thr-Lys-Cys,

Gln-Trp-Cys-Ala-Val-Ser-Gln-Pro-Glu-Ala-Thr-Lys-Cys,

Trp-Cys-Ala-Val-Ser-Gln-Pro-Glu-Ala-Thr-Lys-Cys,

Cys-Ala-Val-Ser-Gln-Pro-Glu-Ala-Thr-Lys-Cys,

Ala-Val-Ser-Gln-Pro-Glu-Ala-Thr-Lys-Cys,

Val-Ser-Gln-Pro-Glu-Ala-Thr-Lys-Cys,

Ser-Gln-Pro-Glu-Ala-Thr-Lys-Cys,

Gln-Pro-Glu-Ala-Thr-Lys-Cys,

Pro-Glu-Ala-Thr-Lys-Cys,

Glu-Ala-Thr-Lys-Cys,

Ala-Thr-Lys-Cys,

Thr-Lys-Cys, and

Lys-Cys,
```

R2 is either no amino acid, Pro or a peptide sequence selected from SEQ ID NO:4 and C-terminally truncated fragments thereof including

```
        Pro-Pro-Val-Ser-Cys-Ile-Lys-Arg,

Pro-Pro-Val-Ser-Cys-Ile-Lys,

Pro-Pro-Val-Ser-Cys-Ile,

Pro-Pro-Val-Ser-Cys,

Pro-Pro-Val-Ser,

Pro-Pro-Val,
        and

Pro-Pro;
```

The above peptide sequences defining R2 thereby being represented by SEQ ID NO: 4 or C-terminally truncated fragments thereof.

In one preferred embodiment X8 is Gly and R3 is Ser-(Arg)$_n$-X9 and the bond α is a peptide bond between the carboxyl group of Gly and the amino group of Ser.

In another preferred embodiment X8 is Lys and R3 is X9-(Arg)$_n$-Ser and the bond α is an amide bond between the ε-amino group in Lys and the carboxyl group in Ser.

In another preferred embodiment X8 is Glu and R3 is Ser-(Arg)$_n$-X9 and the bond α is an amide bond between the γ-carboxyl group of Glu and the amino group of Ser.

In other preferred embodiments amino acid X1 is Gln, X2 is Trp, X3 is Gln or Lys, X4 is Arg, X5 is Asn or Ala, X6 is Met, and/or X7 is Arg.

In another preferred embodiment R1 is either no amino acid or the peptide sequence Ala-Thr-Lys-Cys.

In yet another preferred embodiment R2 is either no amino acid or the peptide sequence Pro-Pro-Val-Ser-Cys-Ile-Lys-Arg.

In one preferred embodiment the present invention provides purified peptides comprising SEQ ID NO: 12 (Phe-Gln-Trp-X3-Arg-X5-Met-Arg-Lys-Val-Arg-Gly-Ser-Arg-Arg-Arg-Arg-Gly), wherein X3 is Gln or Lys and X5 is Asn or Ala, and wherein the peptide is SEQ ID NO: 5, 6, 7, 8, 9, or 10.

When present, it may be advantageous to replace the amino acid Cys by an acetamidomethyl-cysteine in order to avoid that the peptide forms a disulphide bridge with another peptide comprising a cysteine, and/or an intermolecular disulphide bridge if the peptide comprises two Cys residues.

According to one preferred aspect of the invention the carboxy terminal end of the peptide has been capped, i.e. the free COOH at the carboxy terminal end has been transformed into CONH$_2$.

According to another preferred aspect of the invention the amino terminal end of the peptide has been capped, i.e. the free NH$_2$ group at the amino terminal end has been transformed into the amide CH$_3$CONH— (AcNH—).

When the peptides are branched one or both of the amino terminal ends of the peptide can be capped. When the peptides are branched one or both of the carboxy terminal ends of the peptide can be capped.

According to yet another preferred aspect of the invention both the carboxy-terminal and the amino-terminal ends of the peptide have been capped.

The advantage of the capped versions is that N- and C-terminal amino acids of these peptides are neutral and uncharged and thus has changed electrostatic properties. Assuming that the receptors bind the corresponding sequences of human lactoferrin where there are no N- and C terminal charges, the capped peptides should bind better as they in this respect resemble the native protein more than uncapped peptides.

Preferred peptides of the invention are:

Ac-Phe-Gln-Trp-Gln-Arg-Asn-Met-Arg-Lys-Val-Arg-Lys-NH$_2$;
　　　　　　　　　|
　　　　Gly-Arg-Arg-Arg-Ser
Ac-Phe-Gln-Trp-Gln-Arg-Ala-Met-Arg-Lys-Val-Arg-Lys-NH$_2$;
　　　　　　　　　|
　　　　Gly-Arg-Arg-Arg-Ser
Ac-Phe-Gln-Trp-Lys-Arg-Asn-Met-Arg-Lys-Val-Arg-Lys-NH$_2$;
　　　　　　　　　|
　　　　Gly-Arg-Arg-Arg-Ser
Ac-Phe-Gln-Trp-Gln-Arg-Asn-Met-Arg-Lys-Val-Arg-Lys-NH$_2$;
　　　　　　　　　|
　　Ac-Gly-Arg-Arg-Arg-Arg-Arg-Arg-Ser
Ac-Phe-Gln-Trp-Gln-Arg-Asn-Met-Arg-Lys-Val-Arg-Glu-NH$_2$
　　　　　　　　　|
　　　　Ser-Arg-Arg-Arg-Arg-Gly-NH$_2$;
Ac-Phe-Gln-Trp-Gln-Arg-Ala-Met-Arg-Lys-Val-Arg-Glu-NH$_2$
　　　　　　　　　|
　　　　Ser-Arg-Arg-Arg-Arg-Gly-NH$_2$;
Ac-Phe-Gln-Trp-Lys-Arg-Asn-Met-Arg-Lys-Val-Arg-Glu-NH$_2$
　　　　　　　　　|
　　　　Ser-Arg-Arg-Arg-Gly-NH$_2$;
Ac-Phe-Gln-Trp-Lys-Arg-Ala-Met-Arg-Lys-Val-Arg-Glu-NH$_2$
　　　　　　　　　|
　　　　Ser-Arg-Arg-Arg-Arg-Gly-NH$_2$;
Ala-Thr-Lys-CysM-
　-Phe-Gln-Trp-Gln-Arg-Ala-Met-Arg-Lys-Val-Arg-Lys-Pro-Pro-Val-Ser-CysM-Ile-Lys-Arg;
　　　　　　　　　|
　　　　Gly-Arg-Arg-Arg-Arg-Ser
Ac-Phe-Gln-Trp-Gln-Arg-Ala-Met-Arg-Lys-Val-Arg-Lys-Pro-Pro-Val-Ser-CysM-Ile-Lys-Arg;
　　　　　　　　　|
　　　　Gly-Arg-Arg-Arg-Arg-Ser
Ala-Thr-Lys-CysM-
　-Phe-Gln-Trp-Gln-Arg-Ala-Met-Arg-Lys-Val-Arg-Lys-NH$_2$;
　　　　　　　　　|
　　　　Gly-Arg-Arg-Arg-Arg-Ser;
Ala-Thr-Lys-CysM-
　-Phe-Gln-Trp-Lys-Arg-Ala-Met-Arg-Lys-Val-Arg-Lys-Pro-Pro-Val-Ser-CysM-Ile-Lys-Arg;
　　　　　　　　　|
　　　　Gly-Arg-Arg-Arg-Arg-Ser
Ac-Phe-Gln-Trp-Lys-Arg-Ala-Met-Arg-Lys-Val-Arg-Lys-Pro-Pro-Val-Ser-CysM-Ile-Lys-Arg;
　　　　　　　　　|
　　　　Gly-Arg-Arg-Arg-Arg-Ser
Ac-Phe-Gln-Trp-Gln-Arg-Asn-Met-Arg-Lys-Val-Arg-Lys-Pro-Pro-Val-Ser-CysM-Ile-Lys-Arg-NH$_2$
　　　　　　　　　|
　　Ac-Gly-Arg-Arg-Arg-Arg-Arg-Ser
Ala-Thr-Lys-CysM-
　-Phe-Gln-Trp-Lys-Arg-Ala-Met-Arg-Lys-Val-Arg-Lys-NH$_2$;
　　　　　　　　　|
　　　　Gly-Arg-Arg-Arg-Arg-Ser
Ala-Thr-Lys-CysM-
　-Phe-Gln-Trp-Gln-Arg-Ala-Met-Arg-Lys-Val-Arg-Glu-Pro-Pro-Val-Ser-CysM-Ile-Lys-Arg;
　　　　　　　　　|
　　　　Ser-Arg-Arg-Arg-Arg-Gly-NH$_2$
Ac-Phe-Gln-Trp-Gln-Arg-Ala-Met-Arg-Lys-Val-Arg-Glu-Pro-Pro-Val-Ser-CysM-Ile-Lys-Arg;
　　　　　　　　　|
　　　　Ser-Arg-Arg-Arg-Arg-Gly-NH$_2$
Ala-Thr-Lys-CysM-
　-Phe-Gln-Trp-Gln-Arg-Ala-Met-Arg-Lys-Val-Arg-Glu-NH$_2$
　　　　　　　　　|
　　　　Ser-Arg-Arg-Arg-Arg-Gly-NH$_2$;
Ala-Thr-Lys-CysM-
　-Phe-Gln-Trp-Lys-Arg-Ala-Met-Arg-Lys-Val-Arg-Glu-Pro-Pro-Val-Ser-CysM-Ile-Lys-Arg
　　　　　　　　　|
　　　　Ser-Arg-Arg-Arg-Arg-Gly-NH$_2$;
Ac-Phe-Gln-Trp-Lys-Arg-Ala-Met-Arg-Lys-Val-Arg-Glu-Pro-Pro-Val-Ser-CysM-Ile-Lys-Arg
　　　　　　　　　|
　　　　Ser-Arg-Arg-Arg-Arg-Gly-NH$_2$;
Ac-Phe-Gln-Trp-Lys-Arg-Ala-Met-Arg-Lys-Val-Arg-Glu-NH$_2$
　　　　　　　　　|
　　　　Ser-Arg-Arg-Arg-Arg-Arg-Gly-NH$_2$;

Ac-Phe-Gln-Trp-Gln-Arg-Asn-Met-Arg-Lys-Val-Arg-Lys-NH$_2$;
　　　　　　　　　|
　　　　Gly-Arg-Arg-Arg-Arg-Ser
Ac-Phe-Gln-Trp-Lys-Arg-Asn-Met-Arg-Lys-Val-Arg-Lys-NH$_2$;
　　　　　　　　　|
　　　　Gly-Arg-Arg-Arg-Arg-Ser
Ac-Phe-Gln-Trp-Gln-Arg-Asn-Met-Arg-Lys-Val-Arg-Lys-NH$_2$;
　　　　　　　　　|
　　Ac-Gly-Arg-Arg-Arg-Arg-Arg-Ser

```
Ala-Thr-Lys-CysM-
  -Phe-Gln-Trp-Lys-Arg-Ala-Met-Arg-Lys-Val-Arg-Glu-NH₂
                                              |
                                              Ser-Arg-Arg-Arg-Arg-Gly-NH₂;
                                                                              (SEQ ID NO: 5)
Ac-Phe-Gln-Trp-Gln-Arg-Asn-Met-Arg-Lys-Val-Arg-Gly-Ser-Arg-Arg-Arg-Arg-Gly-NH₂;
                                                                              (SEQ ID NO: 6)
Ala-Thr-Lys-CysM-
  -Phe-Gln-Trp-Gln-Arg-Asn-Met-Arg-Lys-Val-Arg-Gly-Ser-Arg-Arg-Arg-Arg-Gly-NH₂;
                                                                              (SEQ ID NO: 7)
Ac-Phe-Gln-Trp-Lys-Arg-Asn-Met-Arg-Lys-Val-Arg-Gly-Ser-Arg-Arg-Arg-Arg-Gly-NH₂;
                                                                              (SEQ ID NO: 8)
Ala-Thr-Lys-CysM-
  -Phe-Gln-Trp-Lys-Arg-Asn-Met-Arg-Lys-Val-Arg-Gly-Ser-Arg-Arg-Arg-Arg-Gly-NH₂;
                                                                              (SEQ ID NO: 9)
Ac-Phe-Gln-Trp-Lys-Arg-Ala-Met-Arg-Lys-Val-Arg-Gly-Ser-Arg-Arg-Arg-Arg-Gly-NH₂;
                                                                              (SEQ ID NO: 10)
Ala-Thr-Lys-CysM-
  -Phe-Gln-Trp-Lys-Arg-Ala-Met-Arg-Lys-Val-Arg-Gly-Ser-Arg-Arg-Arg-Arg-Gly-NH₂;
```

CysM is acetamidomethyl-cysteine.

Where the N-terminally and/or C-terminally capped form of a peptide has been given, it is also possible, according to the invention, to use the un-capped forms.

Where the N-terminally and/or C-terminally un-capped form of a peptide has been given, it is also possible, according to the invention, to use the capped forms.

The sequences Gly-Arg-Arg-Arg-Arg-Arg-Arg-Ser, Gly-Arg-Arg-Arg-Arg-Arg-Ser, Gly-Arg-Arg-Arg-Arg-Ser, Gly-Arg-Arg-Arg-Ser, Ser-Arg-Arg-Arg-Arg-Arg-Gly, Ser-Arg-Arg-Arg-Arg-Gly and Ser-Arg-Arg-Arg-Arg-Gly are positively charged under physiological conditions and are capable of strong and specific interactions with receptors. They are therefore an important part of the peptides according to the invention.

The advantage of the peptides according to the invention is that they comprise the part of the lactoferricin fragment of the human lactoferrin protein, or a modified version thereof, which the inventors have found to be active with regards to the invention.

In some cases only the capped form of a sequence has been given in the appended sequence listing. However, it is also possible, according to the invention, to use the non-capped forms.

Further substitution of active fragments of hLF with an Arg containing peptide resulting in the peptides of the present invention has been shown to provide peptides with improved properties compared to other known peptides derived from hLF.

The peptides according to the invention are suitable for treatment and/or prevention of infections, inflammations, tumours, pain, wounds and scars. The term "treatment" used herein refers to curing, reversing, attenuating, alleviating, minimising, suppressing or halting the deleterious effects of a disease state, disease progression or other abnormal condition, and the term "prevention" used herein refers to minimising, reducing or suppressing the risk of developing a disease state or progression or other abnormal or deleterious conditions.

The infections treatable with the peptides or medicinal products according to the invention include infections caused by all kinds of pathogens, such as bacteria, viruses, fungi, etc.

It is also possible to treat different types of inflammations. Inflammation is a complex phenomenon marked i.a. by abnormal "redness" and swelling of tissues and organs, pain and heat in affected areas, capillary dilation, leucocyte infiltration, etc. Inflammation is primarily caused by exposure to bacterial and other noxious agents and physical injury. Inflammation has many forms and is mediated by a variety of different cytokines and other chemical signals. These mediators of inflammation include tumour necrosis factor-α (TNF-α), interleukin-1 (IL-1), interleukin-6 (IL-6), interleukin-8 (IL-8), and various colony-stimulating factors (CSFs).

As stated above, the peptides according to the invention are also suitable for treatment of tumours.

The peptides according to the invention may either be used as they are or be included in a medicinal product or a pharmaceutical preparation. The medicinal product or a pharmaceutical preparation according to the invention may also comprise substances used to facilitate the production of the pharmaceutical preparation or the administration of the preparations. Such substances are well known to people skilled in the art and may for example be pharmaceutically acceptable adjuvants, carriers and preservatives.

The peptides according to the invention may either be formulated for oral administration, systemic administration, parenteral administration, local administration or topical administration.

The peptides or medicinal products according to the invention can be administered to a patient either orally, systemically, parenterally, locally or topically. The term "patient" used herein relates to any person at risk for or suffering from a disease state, disease progression or other abnormal or deleterious condition.

The systemic administration is suitable e.g. for treatment of urinary tract infection, colitis and tumours. The systemic administration can be undertaken by oral, nasal, intravenous, intraartery, intracavitary, intramuscular, subcutaneous, transdermal, suppositories (including rectal) or other routes known to those of skill in the art. Oral administration is preferred.

The local administration is suitable e.g. for treatment of skin infections, all infections and inflammations in mucosal membranes etc. The local administration can be undertaken by topical, oral, nasal, vaginal or oropharyngeal route. For treatment of local infections or inflammations in the skin or mucosal membranes the peptides or medicinal products according to the invention may e.g. be included in a gel, a cream, an ointment, or a paste.

In the method according to the invention an effective amount of a peptide according to the invention is administered to a patient. The term "effective amount" used herein relates to an amount sufficient to treat or prevent a disease state, disease progression or other abnormal or deleterious conditions.

The peptides or medicinal products and methods according to the invention are particularly well suited for treatment and/or prevention of urinary tract infection and colitis, but several other inflammatory and infectious diseases are also treatable according to the present invention, such as inflammatory bowel diseases, rheumatoid arthritis, conditions caused by the virus HIV-1, conditions caused by the virus CMV, and conditions caused by fungi, e.g. *Candida* species such as *Candida albicans* and *Candida krusei*, *Aspergillus* and *Cryptococcus neoformans*. This listing is in no way limiting the scope of the invention.

The peptides, medicinal products and methods according to the invention are also well suited for preventive medical care by reducing the risk of developing urinary tract infection or other inflammatory or infectious diseases in patients with an increased risk of attracting such complications.

The peptides of the present invention are suited for are anti-inflammatory and immunomodulatory therapies, exemplified but not limited to:

1) Generally, treatment of inflammation and/or medical condition resulting from inflammation, and specifically,
2a) Intestine; Morbus Crohn, Colitis, Ulcerative colitis,
2b) Joints; Rheumatoid arthritis, Arthritis, Arthrosis, Localized disorders of muscles including muscle spasm, muscle tear, muscle injury, muscle strain, muscle sprain,
2c) Dermatology; Psoriasis, Eczema (excema), Dermatitis, Acne
2d) Heart; Pericarditis, Endocarditis Cardiac insufficiency,
2e) Pain; (further specified under 2f below).
2f) Nervous system; Alzheimer, Multiple Sclerosis, Carpal tunnel syndrome, Disc herniation, Cervical rhizopathy, Bells palsy, Acute spinal cord injury, Spinal cord compression, Spinal stenosis, Postherpetic neuralgia, Viral encephalitis, Viral meningitis, Menieres disease, Polio and postpolio complications, Chronic Inflammatory Demyelinating Polyneuropathy, Polyneuropathy, Trigminal neuralgia, Chronic epileptic disorders,
2g) Sensory organs; Glaucoma
2h) Mucosal surfaces (inflammation as a result of chemo/radiation therapy),
2i) Allergy,
2j) Autoimmune diseases The peptides of the invention are further suited for prevention and treatment of wounds and scars in connection with conditions and procedure, exemplified but not limited to:

3a) surgical procedures on various tissues such as skin, muscles, tendons, nervous tissue, blood vessels, and at different locations of the body such as eyes, ears, vocal cord, hand, spinal cord, intra-abdominal cavity, intra-thoracic cavity, intra-cranial cavity, oral cavity, gynecological procedures, endometrios, phimosis,
3b) acne
3c) hypertrophic scars & keloids,
3d) pleuritis,
3e) peritoneal dialysis, The peptides of the invention are further believed to have anti-angiogenetic effects and are therefore suited for treatment of:

4a) Cancer
4b) Rheumatoid arthritis

The peptides of the invention have anti-infectious effects, and are suited for the prevention and treatment of:

5a) Antibacterial Effects:
Upper and lower respiratory tract (tonsillitis, sinusitis etc.)
Infections of the eye (e.g. conjunctivitis)
Urinary tract infections
Sexually transmitted diseases (including antimicrobial coating of condomes)
Genital tract including vaginosis, vaginitis, cervicitis, endometritis, PID
Gastrointestinal tract infections (systemic infections initiated in the GI)
Central nervous system infections
Infections of the skin (including staphylococci, for instance MRSA, nosocomial, wounds, burns), muscle, joints (e.g. septic arthritis), bone and hemopoietic system
Infections related to the mouth, including parodontitis, gingivitis 5b) Antiviral Effects:
Upper and lower respiratory tract
Sexually transmitted diseases
Gastrointestinal tract infections (systemic infections initiated in the GI)
Central nervous system infections 5c) Antifungal effects:
Upper and lower respiratory tract (such as aphthae, mucocutanous candidiasis)
Genitourinary tract, such as vulvovaginal candidiasis, balanitis,
Gastrointestinal tract infections (systemic infections initiated in the GI)
Central nervous system infections
Infections of the skin (such as mucocutanous candidiasis)

The peptides, medicinal products and methods according to the invention may either be used alone, in combination with each other or in combination with conventional therapy.

According to the present invention it is also possible to include the peptides, in an effective amount, in any kind of food or beverage intended to reduce infections and/or inflammations in patients running an increased risk of such conditions due to an underlying disease, a low birth weight or a medical treatment. For example, it is possible to include the peptides, in an effective amount, in an infant formula food intended to inhibit harmful effects of bacteria, such as weight loss caused by inflammation induced by bacteria, viruses or fungi in infants. When the peptides according to the invention is to be used in food stuffs, e.g. for nutritional purposes, it is especially preferred to use peptides of natural origin.

Since the peptides according to the invention have antimicrobial effects they can also be used as preservatives in different food stuffs and medicinal products such as gels, creams, ointments, pastes, solutions, emulsions etc.

The invention will now be further explained in the following examples. These examples are only intended to illustrate the invention and should in no way be considered to limit the scope of the invention.

EXAMPLES

Example 1

Antimicrobial Assay

Arg-Arg-Arg-Arg- or Arg-Arg-Arg-containing peptides (Table 1) have been analysed by an antimicrobial assay using E. coli, S. aureus and C. albicans as test microorganisms.

Washed cells were suspended in 1% Bactopeptone (BP) (Difco, USA). The concentration of bacterial or fungal cells was spectrophotometrically adjusted. Peptides serially diluted in BP by twofold steps were added in duplicate or triplicate to the wells of a microtiterplate (200 µl per well). The bacterial or yeast cell solutions were added in 10 µl volumes to give a final concentration of approximately $2 \times 10^5$ cells per ml. The concentration of the stock solution was always checked by viable counts. The microplate was incubated at 37° C. in a humid chamber for 2 h unless otherwise stated. Five µl were taken from each well and added as a drop onto a blood agar plate and incubated over night at 37° C.

The concentration of lactoferrin or peptide causing a 99% reduction of the inoculum was defined as the $MMC_{99}$.

The microbicidal activity of the peptides showed that all peptides were better than the natural sequence amino acids 1-31 (HLBD31) except for HLBDarg2 (Table 2). In this peptide the Arg-Arg-Arg-Arg-Arg sequence was linked to phenylalanine from the amino-terminal side via a spacer (three glycine residues).

Figure 1:
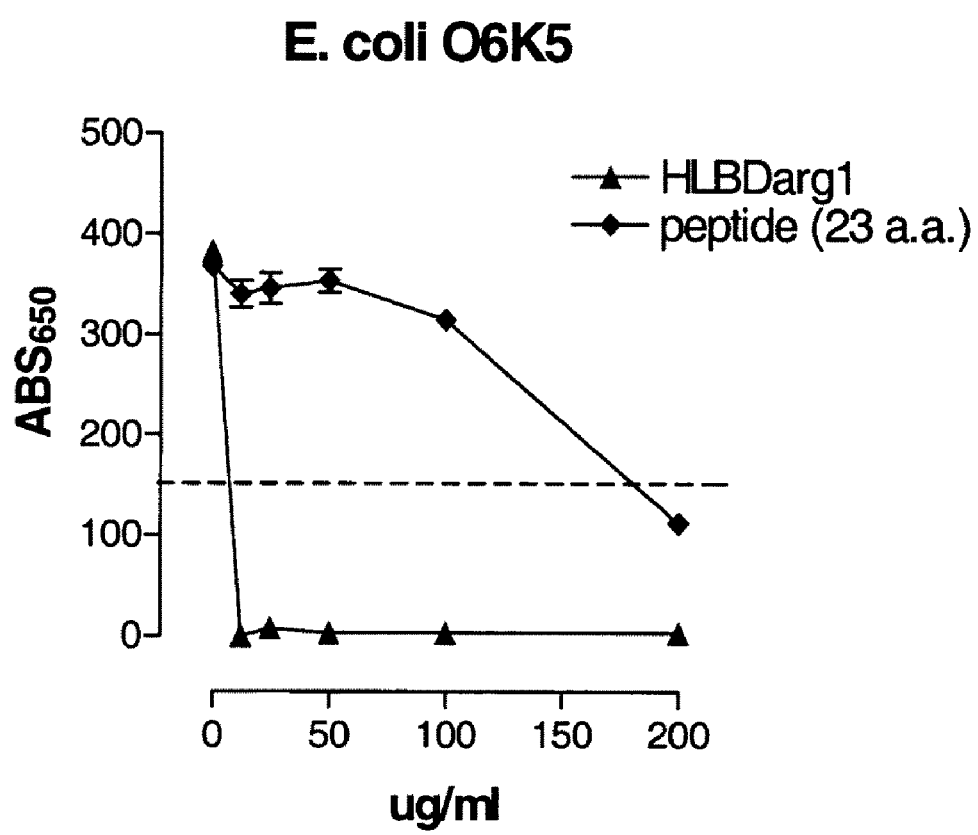
FIG. 1. Growth inhibition of *E. coli* in the presence of HLBDarg1 and a 23-a.a. long peptide (amino acids 18 to 40 of hLF). Using a peptone medium (1%) the microplate was incubated over night and read spectrophotometrically at 650 nm. As can be seen a concentration of 12.5 µg/ml totally reduced the growth.

In FIG. 1 the growth inhibition of HLBDarg1 was compared with a native lactoferrin-derived peptide HLBD2 consisting of amino acids 18 to 40. A much stronger antimicrobial activity was recorded for HLBDarg1 in this medium which strongly reduces the antimicrobial activity of many other LF derived peptides.

TABLE 1

Arginine-tailed peptides used in the Examples

| Peptide | Sequence |
|---|---|
| HLBD Arg1 | Ac- F Q W Q R N M R K V R K -NH₂<br>                                  G R R R S |
| HLBD Arg1 rak | Ac- F Q W Q R N M R K V R G S R R R R G -NH₂ |
| HLBD Arg2 | G R R R S G G G F Q W Q R N M R K V R |
| HLBD Arg5 | Ac- F Q W Q R N M R K V R K -NH₂<br>                                  G R R R S |
| HLBD Arg1optC | Ac- F Q W Q R A M R K V R K -NH₂<br>                                  G R R R S |
| HLBD Arg1optC(K24) | Ac- F Q W K R A M R K V R K -NH₂<br>                                  G R R R S |
| HLBD2 optC Arg1 | A T K Cm F Q W Q R A M R K V R K P P V S Cm I K R<br>                                                        G R R R S |

TABLE 1-continued

Arginine-tailed peptides used in the Examples

| Peptide | Sequence |
|---|---|
| HLBD31 | G R R R R S V Q W C A V S Q P E<br>A T K Cm F Q W Q R N M R K V R |
| PXL11 | Ac- F Q W Q R N M R K V R K -NH$_2$<br>Ac- G R R R R R S |
| PXL12 | Ac- F Q W Q R N M R K V R K -NH$_2$<br>Ac- G R R R R R R S |
| PXL13 | Ac- F Q W K R A M R K V R E -NH$_2$<br>S R R R R R R -NH$_2$ |
| PXL14 | Ac- F Q W Q R N M R K V R K P P V S Cm I K R -NH$_2$<br>Ac- G R R R R R S |

Cm is acetamidomethyl-cysteine

TABLE 2

| | MMC$_{99}$, µg/ml | | | | | |
|---|---|---|---|---|---|---|
| | C. albicans | | S. aureus | | E. coli | |
| peptide | 2 h | 24 h | 2 h | 24 h | 2 h | 24 h |
| HLBDarg1 | 6.3 | 10 | 12 | 19 | 17 | 3.1 |
| HLBDarg5 | 12 | 12 | 25 | 25 | 25 | 6 |
| HLBDarg1optC | 12 | 21 | 25 | 25 | 19 | 6 |
| HLBDarg1optC(K24) | ≦50 | ≦50 | 16 | 12 | 12 | 6 |
| HLBD2optCarg1 | 12 | 25 | 25 | 25 | 25 | 12 |
| HLBDarg1rak | ND | ND | 12 | 19 | 12 | 6 |
| HLBDarg2 | >100 | >100 | >100 | >100 | >100 | >100 |
| HLBD31 | 25 | 38 | 100 | 100 | >100 | 50 |

*ND = not determined

Example 2

*Staphylococcus aureus* Joint Infection

Mice. 5 to 8-week old mice were obtained from B&K (Sollentuna, Sweden) and maintained in the animal facility of the Department of Rheumatology, University of Göteborg. They were housed 10 per cage under standard conditions of temperature, and light and fed standard chow and water ad libitum.

Bacterial strain and infection. *S. aureus* strain AB-1 was used. The bacteria were injected into the both knee joints (synovial space) of the hind paw. Immediately before injection, bacteria and peptide or vehicle only were mixed. A dose of $2 \times 10^4$ *S. aureus* and 100 µg of peptide (HLBDarg1) were injected. The knee of the right hind paw was used as positive control. Also some animals were injected with peptide solution only. The animals were killed at day 3 after infection and the knee joints were fixed in formaline and decalcified for histological evaluation. The number of bacteria present in the left joint was analysed by culturing (cotton swab of joint fluid after removal of skin).

Figure 2:
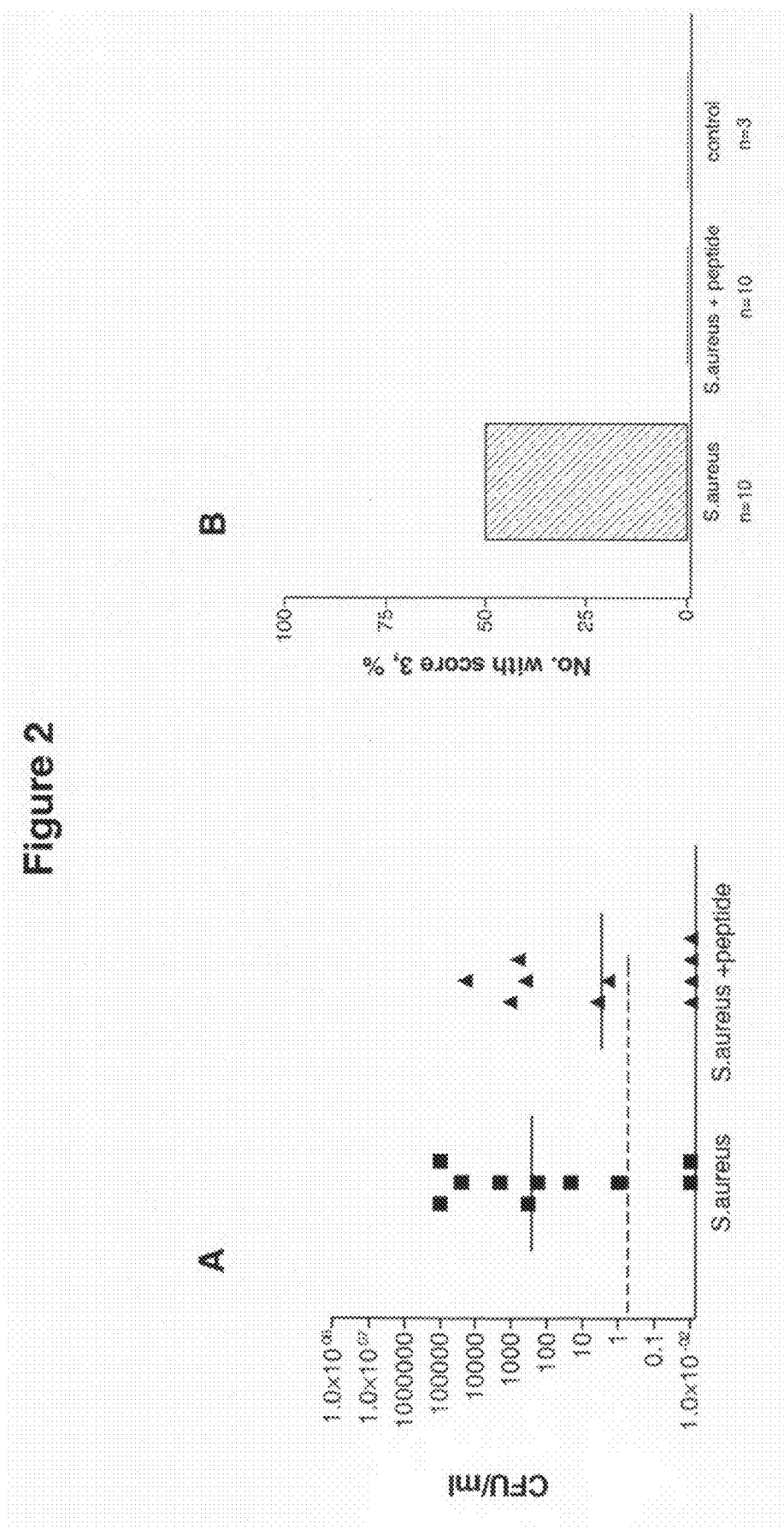
FIG. 2. A) The number of *S. aureus* located in the joints of peptide-treated and vehicle treated animals. B) The distribution of animals with a scoring of 3 or more (the most severe inflammation and/or erosion of joint tissue was scored as 5, and no histological changes as 0). A dose of $2\times10^4$ *S. aureus* and 100 µg of peptide (HLBDarg1) were injected.

The numbers of *S. aureus* in the joint were higher in the vehicle treated group although no statistical significance was established (FIG. 2). The blind scoring of the joints revealed significant differences between peptide-treated and vehicle treated animals. Thus the peptide appeared to reduce the severity of the *Staphylococcus*-induced arthritis.

Example 3

*Candida albicans* Skin Infection

*Candida albicans*. The yeast cells (ATCC64549) were incubated over night in Sabourad broth at 23° C. The cells were washed in phosphate buffer (10 mM, pH 7.4) and adjusted to a concentration of $2 \times 10^{10}$/ml.

Figure 3:
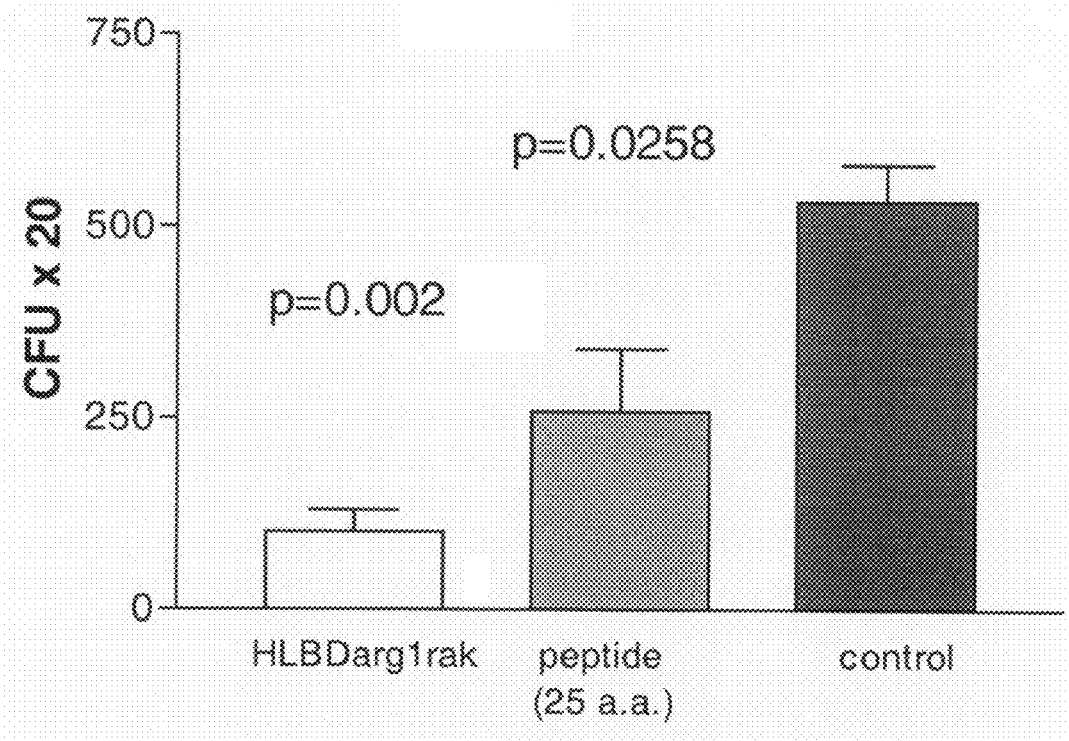
FIG. 3. Effects of peptide treatment in *Candida* skin infection (quadruple spots for each peptide). The treatment dose was 400 µg per infected area. The arginine containing peptide reduced *C. albicans* to a higher degree than a longer peptide sequence based on the antimicrobial region in LF (peptide 25 a.a.=peptide corresponding to amino acids 16-40 of hLF).

Skin infection and peptide treatment. Mice were treated with *C. albicans* on a shaved area ($2 \times 10^8$ yeast cells per spot) by gentle rubbing a volume of 10 µl with a blunt plastic rod during anaesthesia. The following day anaesthetized mice were treated with 10 or 20 µl of a peptide solution or vehicle (phosphate buffer) by applying the volume onto the infected spots. The solution was allowed to dry. After 4 h the treatment was repeated. The day after the animals were killed. Viable counts were performed on washings, obtained from the treated areas by using a metal ring placed over the spot and gentle rubbing in the presence of 100 µl of phosphate buffer containing Triton-x 100 (0.01%). At most three different concentrations of the peptide were used, starting with 400, 100, and 25 µg per spot. Although a high variability was obtained (quadruple spots for each concentration), a clear reduction of colony-forming units (CFU) is obtained with the three peptides (Table 3). The results obtained with 400 µg are presented in FIG. 3.

TABLE 3

| | | Candida albicans | | |
|---|---|---|---|---|
| peptide | no. of experiments | CFU (mean ± SE) treatment | CFU (mean ± SE) vehicle | p value |
| HLBDarg1 | 3 | 40 ± 10 | 166 ± 33 | 0.0066 |
| HLBDarg1rak | 2 | 105 ± 28 | 414 ± 60 | 0.0004 |
| HLBDarg5 | 1 | 12 ± 8.3° | 43 ± 3 | 0.024 |

°1 mg per spot

Example 4

In Vitro Anti-Inflammatory and Fibrinolytic Effect

The MeT-5A cell line corresponding to normal human mesothelial cells was maintained in M199 medium (GIBCO)

supplemented with 10% fetal bovine serum (FBS; PAA Laboratories GmbH), 3.3 nM epidermal growth factor (EGF; AMS Biotechnology Ltd), 400 nM hydrocortisone (MP Biomedicals), 20 mM Hepes (PAA Laboratories GmbH) and 870 nM human recombinant insulin (Sigma). The cells were induced by addition of recombinant IL-1 (R&D Systems), 0.1 or 0.5 ng/ml in the case of the IL-6 or PAI-1 assay, respectively, into the medium specified above except of containing 5% heat inactivated FBS. The given concentration of peptide HLBD1 Arg rak was added immediately after stimulation by IL-1.

IL-6 production was measured 3 hours after induction by quantitative immunoassay ELISA using human monoclonal anti-IL-6 antibody (R&D Systems).

PAI-1 levels were measured 6 hours after induction by commercially available ELISA kit (Tint-Eliza PAI-1, Trinity Biotech).

The results are expressed in relation to the IL-6 (288 pg/ml) or PAI-1 levels (18.3 ng/ml) obtained without any peptide added.

Figure 4:
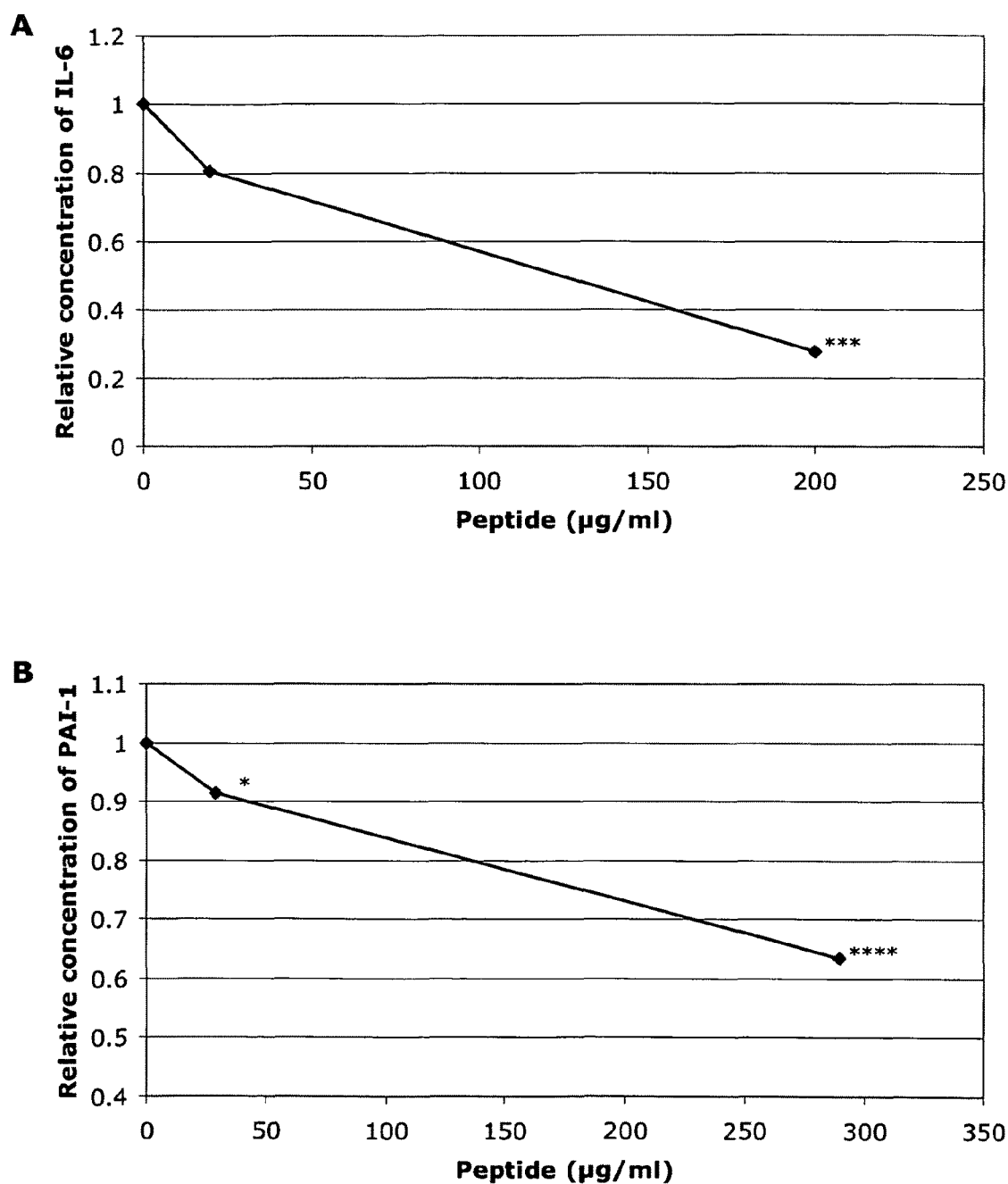
FIG. 4. Inhibitory activity of a lactoferrin-derived (HLBD1 Arg rak) peptide on IL-1-induced IL-6 (A) or PAI-1 (B) production in MeT-5A cells. Indicated peptide concentrations were added to cells in triplicate (n=3) immediately after the addition of IL-1, the cell supernatants were collected after 3 hours (in A) or 6 hours (in B) of incubation and analyzed for IL-6 (in A) or PAI-1 (in B) by quantitative ELISA. The results are expressed in relation to the IL-6 level (288 pg/ml) or PAI-1 level (18.3 ng/ml) obtained without any peptide added, respectively. Statistical differences were determined by two-sided Student's t-test (* $p \leq 0.05$;  $p \leq 0.01$; * $\leq p0.005$; **** $\leq p0.001$).

The results (FIG. 4) indicate that IL-6 and PAI-1 production in mesothelial cells is significantly down regulated by the peptide.

Example 5

In Vitro Anti-Inflammatory Effect

The THP-1 cell line (ATCC #TIB-202) corresponding to human monocytes was maintained in RPMI 1640 (PAA Laboratories GmbH) supplemented with 10% fetal bovine serum (FBS; PAA), 1 mM Sodium Pyruvate (Sigma), and 20 mM HEPES (PAA). The cell density was adjusted to $1 \times 10^6$ cells/ml and 500 µl of the cell suspension was added to 24-well cell culture plates (Sarstedt). The cells were treated with 10 ng/ml PMA (phorbol 12-myristate 13-acetate; Sigma) for 48 hours to differentiate the monocytes into macrophage-like cells. After 48 hours the cells were stimulated by addition of 0.1 ng/ml LPS (E. coli serotype 055:B5; Sigma) into the medium specified above except of containing 5% heat inactivated FBS. The given concentration of peptide HLBD1 Arg rak was added 30 minutes after addition of LPS. The cell supernatants were collected after 6 hours of incubation, centrifuged and analyzed for TNF-α production by ELISA (R&D Systems).

Figure 5:
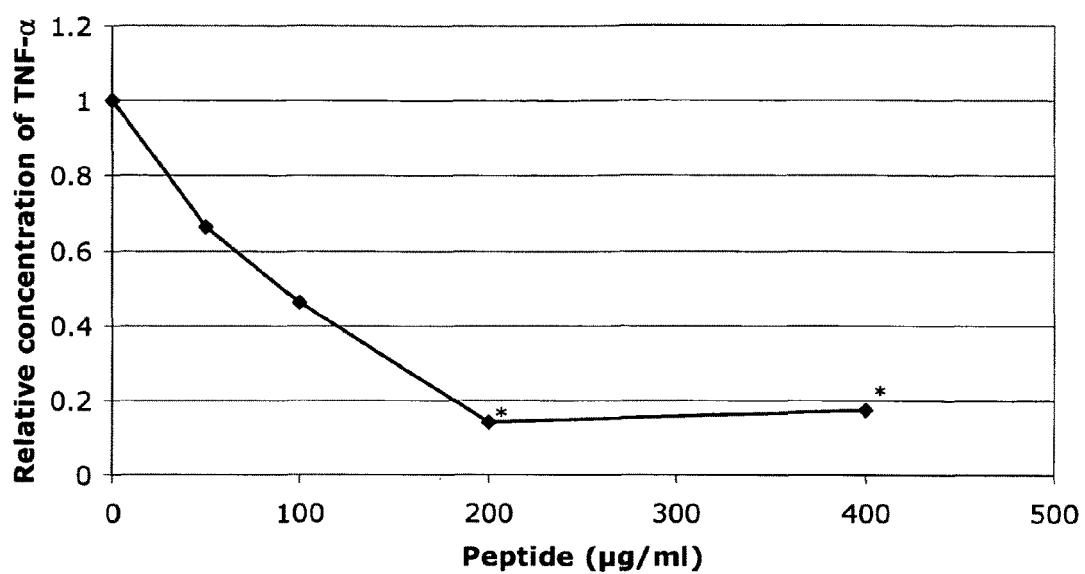
FIG. 5. Dose-inhibitory activity of a lactoferrin-derived peptide (HLBD1 Arg rak) on LPS-induced TNF-α secretion in human monocyte derived macrophage cell line THP-1 cells. Indicated peptide concentrations were added to cells in triplicate (n=3) 30 min after the addition of LPS (0.1 ng/ml). TNF-α levels at 6 h after the stimulation were measured by ELISA (R&D Systems, Minneapolis, Minn.). The results are expressed in relation to TNF-α levels (290 µg/ml) obtained without any peptide added. Statistical differences among genotypes were determined by two-sided Student's t-test (* $p \leq 0.05$).

The results (FIG. 5) of the experiment demonstrate that TNF-α production in human monocyte derived macrophages is significantly down regulated by the peptide.

Example 6

In Vitro Anti-Inflammatory and Fibrinolytic Effect

The MeT-5A cell line corresponding to normal human mesothelial cells was maintained in M199 medium (GIBCO) supplemented with 10% fetal bovine serum (FBS; PAA Laboratories GmbH), 3.3 nM epidermal growth factor (EGF; AMS Biotechnology Ltd), 400 nM hydrocortisone (MP Biomedicals), 20 mM Hepes (PAA Laboratories GmbH) and 870 nM human recombinant insulin (Sigma). The cell density was adjusted to $1.6 \times 10^5$ cells/ml and 100 µl of the cell suspension was added per well to 96-well cell culture plates (Sarstedt). The cells were incubated for 48 hours to allow cells to attach and grow to confluence. After 48 hours the cells were induced by addition of recombinant IL-1β (R&D Systems), 0.1 or 0.5 ng/ml in the case of the IL-6 or PAI-1 assay, respectively, into the medium specified above except of containing 5% heat inactivated FBS. The given concentrations of the different peptides were added immediately after stimulation by IL-1β.

The cell supernatants were collected after 3 or 6 hours of incubation and analyzed for IL-6 or PAI-1 by ELISAs specific for IL-6 (R&D Systems) or for PAI-1 (Tint-Eliza PAI-1, Trinity Biotech), respectively.

Figure 6:
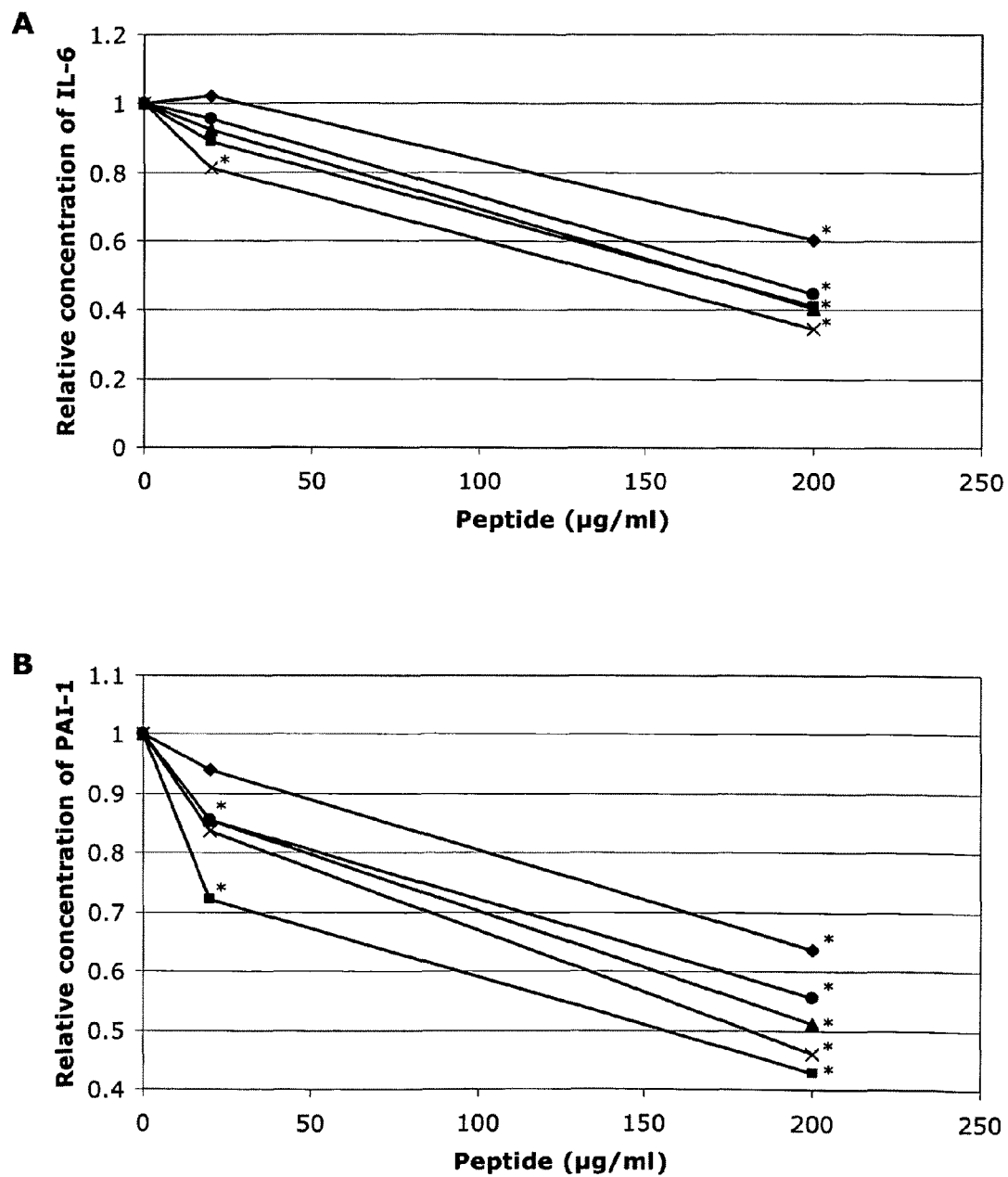
FIG. 6. Dose-inhibitory activity of lactoferrin-derived peptides on IL-1β-induced IL-6 (A) or PAI-1 (B) production in MeT-5A cells. Indicated peptide concentrations were added to cell in triplicate (n=3) immediately after the addition of IL-1β, the cell supernatants were collected after 3 hours (in A) or 6 hours (in B) of incubation and analyzed for IL-6 (in A) or PAI-1 (in B) by quantitative ELISA. The results are expressed in relation to the IL-6 level (1770 pg/ml) or PAI-1 level (63.0 ng/ml) obtained without any peptide added. Statistical differences were determined by two-sided Student's t-test (* $p \leq 0.05$;). ♦=HLBDarg1rak, ▲=PXL11, x=PXL12, ■=PXL13, ●=PXL14.

The results (FIG. 6) indicate that IL-6 and PAI-1 production in mesothelial cells is significantly down regulated by the peptides.

Example 7

In Vitro Anti-Inflammatory Effect

The THP-1 cell line (ATCC #TIB-202) corresponding to human monocytes was maintained in RPMI 1640 (PAA Laboratories GmbH) supplemented with 10% fetal bovine serum (FBS; PAA), 1 mM Sodium Pyruvate (Sigma), and 20 mM HEPES (PAA). The cell density was adjusted to $1 \times 10^6$ cells/ml and 100 µl of the cell suspension was added per well to 96-well cell culture plates (Sarstedt). The cells were treated with 10 ng/ml PMA (phorbol 12-myristate 13-acetate; Sigma) for 48 hours to differentiate the monocytes into macrophage-like cells. After 48 hours the cells were stimulated by addition of 0.1 ng/ml LPS (E. coli serotype O55:B5; Sigma) into the medium specified above except of containing 5% heat inactivated FBS. The indicated concentrations of the different peptides were added 30 min after addition of LPS. The cell supernatants were collected after 6 hours of incubation, centrifuged and analyzed for TNF-α production by ELISA (R&D Systems).

Figure 7:
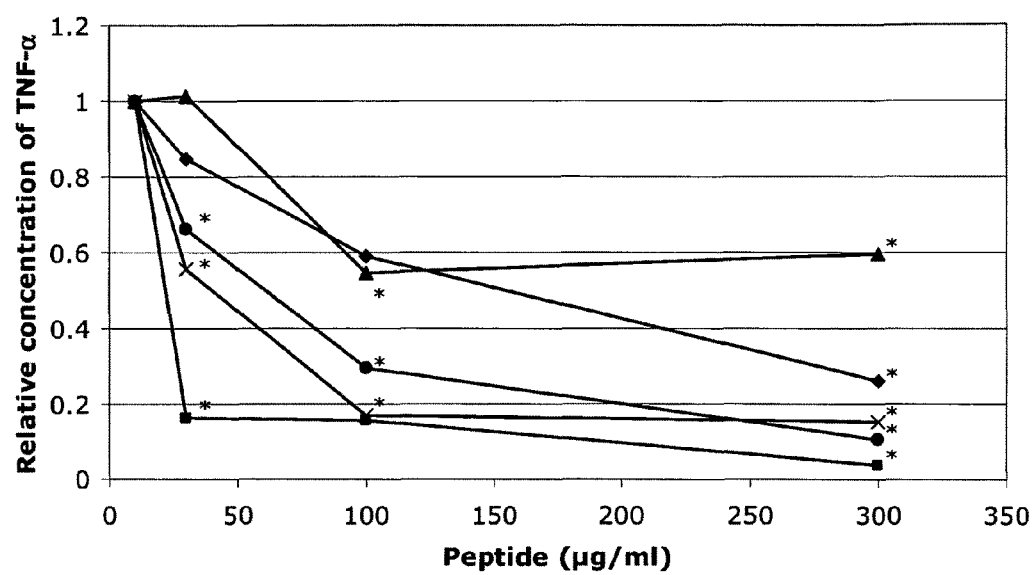
FIG. 7. Dose-inhibitory activity of lactoferrin-derived peptides on LPS-induced TNF-α secretion in human monocyte derived macrophage cell line THP-1 cells. Indicated peptide concentrations were added to cells in triplicate (n=3) 30 min after the addition of LPS (0.1 ng/ml). TNF-α levels at 6 h after the stimulation were measured by ELISA (R&D Systems). The results are expressed in relation to TNF-α levels (273-775 pg/ml) obtained with peptide added at 10 µg/ml. Statistical differences were determined by two-sided Student's t-test (* $p \leq 0.05$;). ♦=HLBDarg1rak, ▲=PXL11, x=PXL12, ■=PXL13, ●=PXL14.

The results (FIG. 7) of the experiment demonstrate that TNF-α production in human monocyte derived macrophages is significantly down regulated by the peptides.

Example 8

Antimicrobial Assay

Arg-Arg-Arg-Arg-Arg-Arg- or Arg-Arg-Arg-Arg-Arg-containing peptides (Table 4) have been analysed by an antimicrobial assay using E. coli, S. aureus and P. aeruginosa as test microorganisms.

Cells were suspended in 1% Brain-heart infusion medium (BHI) (Difco, USA). The concentration of bacterial cells was spectrophotometrically adjusted. Peptides serially diluted in 1% BHI by twofold steps were added in duplicate to the wells of a microtiterplate (100 µl per well). The bacterial solutions were added in 5 µl volumes to give a final concentration of approximately $5 \times 10^5$ cells per ml. The concentration of the stock solution was always checked by viable counts. The microtiterplate was incubated at 37° C. for two hours. Five µl were taken from each well and added as a drop onto a blood agar plate and incubated over night at 37° C.

The concentration of peptide causing a 99% reduction of the inoculum was defined as the $MMC_{99}$.

TABLE 4

| | $MMC_{99}$, µg/ml | | |
|---|---|---|---|
| peptide | S. aureus | E. coli | P. aeruginosa |
| PXL11 | 6.3 | 1.6 | 3.1 |
| PXL12 | 6.3 | 1.6 | 3.1 |
| PXL13 | 6.3 | 1.6 | 6.3 |
| PXL15 | 6.3 | 1.6 | 3.1 |
| HLBDarg1rak | 6.3 | 3.1 | 6.3 |

The invention claimed is:

1. A purified peptide comprising SEQ ID NO: 12 (Phe-Gln-Trp-Xaa-Arg-Xaa-Met-Arg-Lys-Val-Arg-Gly-Ser-Arg-Arg-Arg-Arg-Gly), wherein the amino acid Xaa at position 4 of SEQ ID NO: 12 is Gln or Lys, and the amino acid Xaa at position 6 of SEQ ID NO: 12 is Asn or Ala, and wherein the peptide is SEQ ID NO: 5, 6, 7, 8, 9, or 10.

2. A peptide according to claim 1, wherein the free COOH at the carboxy terminal end has been transformed into $CONH_2$.

3. A peptide according to claim 1, wherein the free $NH_2$ group at the amino terminal end has been transformed into the amide $CH_3CONH$.

4. A peptide according claim 1, wherein the amino acid Cys, if present, has been replaced by an acetamidomethyl-cysteine.

5. A pharmaceutical composition comprising a peptide according to claim 1.

6. A pharmaceutical composition according to claim 5 formulated for systemic, parenteral, local or topical administration.

7. A method for treatment of wounds wherein an effective amount of a peptide according to claim 1 is administered to a patient.

8. A method according to claim 7, wherein the substance is systemically, parenterally, locally or topically administered.

* * * * *